US009656929B2

(12) United States Patent
Abdelghani (10) Patent No.: US 9,656,929 B2
(45) Date of Patent: May 23, 2017

(54) CO-EXTRACTION SYSTEMS FOR SEPARATION AND PURIFICATION OF BUTADIENE AND ISOPRENE

(71) Applicant: SAUDI BASIC INDUSTRIES CORPORATION, Riyadh (SA)

(72) Inventor: Mohamed Sabri Abdelghani, Riyadh (SA)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 0 days.

(21) Appl. No.: 14/892,277

(22) PCT Filed: Jun. 19, 2014

(86) PCT No.: PCT/IB2014/062458
§ 371 (c)(1),
(2) Date: Nov. 19, 2015

(87) PCT Pub. No.: WO2014/203207
PCT Pub. Date: Dec. 24, 2014

(65) Prior Publication Data
US 2016/0122265 A1    May 5, 2016

Related U.S. Application Data

(60) Provisional application No. 61/836,799, filed on Jun. 19, 2013, provisional application No. 61/929,677, filed on Jan. 21, 2014.

(51) Int. Cl.
*C07C 7/00* (2006.01)
*C07C 7/04* (2006.01)
(Continued)

(52) U.S. Cl.
CPC ............... *C07C 7/10* (2013.01); *B01D 3/143* (2013.01); *B01D 11/0488* (2013.01);
(Continued)

(58) Field of Classification Search
CPC . B01D 3/00; B01D 3/14; B01D 3/143; B01D 11/00; B01D 11/04; B01D 11/0488;
(Continued)

(56) References Cited

U.S. PATENT DOCUMENTS 2,768,224 A    10/1956  Page et al.
2,971,036 A     2/1961  James
(Continued)

FOREIGN PATENT DOCUMENTS

| DE | 2724365 A1 | 11/1978 |
| EP | 1083160 B1 | 7/2005 |
| JP | 63101338 A * | 5/1988 |

OTHER PUBLICATIONS

Kim et al., Simulation of 1,3-butadiene extractive distillation process using N-methyl-2-pyrrolidone solvent, 2012, Korean J. Chem. Eng., 29(11, 1493-1499.*
(Continued)

*Primary Examiner* — Natasha Young
(74) *Attorney, Agent, or Firm* — Cantor Colburn LLP (57) ABSTRACT

Co-extraction techniques for separating and purifying butadiene and isoprene from a $C_4$ hydrocarbon mixture including butadiene and a $C_5$ hydrocarbon mixture including isoprene are provided. In an exemplary embodiment, a system includes a dimerization heat exchanger, a $C_5$ purification column; an extraction zone including a mainwasher column, a rectifier column and an afterwasher column; a distillation zone; a degassing zone; and an isoprene finishing column. The system can further include a $C_5$ washer column, an absorption column, and a distillation column.

19 Claims, 4 Drawing Sheets

(51) Int. Cl.
| | | |
|---|---|---|
| *C07C 7/05* | (2006.01) | |
| *C07C 7/08* | (2006.01) | |
| *C07C 7/10* | (2006.01) | |
| *C07C 11/00* | (2006.01) | |
| *C07C 11/12* | (2006.01) | |
| *C07C 11/16* | (2006.01) | |
| *C07C 11/167* | (2006.01) | |
| *C07C 11/173* | (2006.01) | |
| *C07C 11/18* | (2006.01) | |
| *B01D 3/14* | (2006.01) | |
| *B01D 11/04* | (2006.01) | |
| *B01D 19/00* | (2006.01) | |
| *B01D 3/00* | (2006.01) | |
| *B01D 11/00* | (2006.01) | |

(52) U.S. Cl.
CPC ...... *B01D 11/0492* (2013.01); *B01D 19/0068* (2013.01); *C07C 7/005* (2013.01); *C07C 7/04* (2013.01); *C07C 7/08* (2013.01)

(58) Field of Classification Search
CPC ................ B01D 11/0492; B01D 19/00; B01D 19/0068; C07C 7/00; C07C 7/005; C07C 7/04; C07C 7/05; C07C 7/08; C07C 7/10; C07C 11/00; C07C 11/12; C07C 11/16; C07C 11/167; C07C 11/173; C07C 11/18
See application file for complete search history.

(56) References Cited

U.S. PATENT DOCUMENTS

| | | |
|---|---|---|
| 3,436,438 A | 4/1969 | Takao et al. |
| 3,692,861 A | 9/1972 | Akimoto et al. |
| 4,162,198 A | 7/1979 | Stockburger et al. |
| 4,232,182 A * | 11/1980 | Liakumovich .......... C07C 7/005 585/627 |
| 4,310,388 A | 1/1982 | Volkamer et al. |
| 6,337,429 B1 | 1/2002 | Kindler et al. |
| 6,395,953 B1 | 5/2002 | Koga et al. |
| 6,958,426 B2 | 10/2005 | Tian et al. |
| 2008/0257711 A1 | 10/2008 | Chen et al. |

OTHER PUBLICATIONS

Grub et al., Butadiene, Wiley-VCH Verlag GmbH & Co. KGaA, Ullmann's Encyclopedia of Industrial Chemistry, vol. 6, 381-396.*
Machine translation of JP 63-101338 A, which was published on May 6, 1988.*
Butadiene Extraction Technology; Chicago Bridge & Iron Company; 2012, 2 pages.
German Patent No. 2724365; Date of Publication: Nov. 30, 1978; Abstract Only, 2 pages.
International Search Report for International Application No. PCT/IB2014/062458; Date of Mailing: Oct. 22, 2014; 2 pages.
The manufacture of Isoprene from C5 Cracking Fractions; Lookchem.com, Accessed 2013; 2 pages.
Written Opinion of the International Searching Authority for International Application No. PCT/IB2014/062458; Date of Mailing: Oct. 22, 2014; 5 pages.

* cited by examiner

CO-EXTRACTION SYSTEMS FOR SEPARATION AND PURIFICATION OF BUTADIENE AND ISOPRENE

CROSS REFERENCE TO RELATED APPLICATIONS

This application is a National Stage application of PCT/IB2014/062458, WO 2014/203207, filed on Jun. 19, 2014, which claims the benefit of U.S. Provisional Application No. 61/836,799, filed, Jun. 19, 2013, and U.S. Provisional Application No. 61/929,677, filed Jan. 21, 2014, both of which are incorporated by reference in their entirety herein.

FIELD

The presently disclosed subject matter relates to co-extraction systems and processes for separating and purifying butadiene and isoprene from $C_4$ and $C_5$ hydrocarbon mixtures.

BACKGROUND

Certain technologies for extracting isoprene from a $C_5$ hydrocarbon mixture and/or butadiene from a $C_4$ hydrocarbon mixture are known in the art. For example, U.S. Pat. No. 6,395,953 and U.S. Patent Publication No. 2008/0257711 disclose a process for producing a purified conjugated diene (e.g., isoprene or butadiene) from a petroleum fraction (e.g., a $C_4$ hydrocarbon fraction or $C_5$ hydrocarbon fraction) by extractive distillation. U.S. Pat. No. 4,310,388 describes a process for isolating a conjugated diolefin from a $C_4$- or $C_5$-hydrocarbon mixture by extractive distillation with the aid of a selective solvent. U.S. Pat. No. 3,692,861 discloses a process for separating and purifying isoprene from a $C_5$ hydrocarbon fraction. U.S. Pat. No. 3,436,438 discloses a process of removing acetylenes from a hydrocarbon mixture containing conjugated diolefins (e.g., isoprene or 1,3-butadiene) by using a solvent.

Two or more extraction systems can be required to extract both butadiene and isoprene, with resulting increases in capital cost, utilities, and land usage.

There remains a need in the art for a co-extraction system that can extract both butadiene and isoprene in one system rather than separate systems.

SUMMARY

The presently disclosed subject matter provides co-extraction techniques for separating and purifying butadiene and isoprene from a $C_4$ hydrocarbon mixture including butadiene and a $C_5$ hydrocarbon mixture including isoprene. In an exemplary embodiment, a system includes a $C_5$ purification column to receive a $C_5$ hydrocarbon mixture including isoprene and separate the light ends of the $C_5$ hydrocarbon mixture from the heavy ends ($C_5$+) hydrocarbons. The system can further include an extraction zone, a distillation zone, a degassing zone, and an isoprene finishing column to receive a crude isoprene product, where isoprene is purified from the crude isoprene product.

In non-limiting embodiments of the presently disclosed subject matter, the extraction zone can include a mainwasher column to receive the light ends of the $C_5$ hydrocarbon mixture, a $C_4$ hydrocarbon mixture including butadiene, and an extractive solvent. Butadiene and isoprene can be co-extracted from the $C_4$ and $C_5$ hydrocarbon mixtures by using the extractive solvent to provide a crude butadiene product, $C_4$ acetylenes, and a crude isoprene product. The crude butadiene product can include 1,3-butadiene and 1,2-butadiene, cis-2-butene, and trans-2-butene. 1,3-butadiene can be present in a greater amount than 1,2-butadiene, cis-2-butene, and trans-2-butene. The crude isoprene product can include isoprene and 1-pentene. Isoprene can be present in a greater amount than 1-pentene. The extraction zone can also include a rectifier column to receive the crude butadiene product, the crude isoprene product, the extractive solvent, and the $C_4$ acetylenes. The crude butadiene product can be separated from the crude isoprene product, the extractive solvent and the $C_4$ acetylenes in the rectifier column.

In certain embodiments, the extractive solvent can be an aqueous solution of n-methyl 2-pyrrolidone having about 91.7% by weight of n-methyl 2-pyrrolidone and about 8.3% by weight of water. In certain embodiments, the extraction zone can further include an afterwasher column coupled to the rectifier column to remove acetylene traces present in the crude butadiene product by using a solvent. The solvent can be n-methyl 2-pyrrolidone.

In non-limiting embodiments of the presently disclosed subject matter, the distillation zone includes a butadiene finishing column to receive the crude butadiene product, where 1,3-butadiene is purified from the crude butadiene product. In some embodiments, the crude butadiene product recovered from the afterwasher column includes propyne. Thus, the distillation zone can further include a propyne column coupled to the afterwasher column to separate propyne from the crude butadiene product.

In non-limiting embodiments of the presently disclosed subject matter, the degassing zone includes a degasser column to receive the crude isoprene product, the extractive solvent, and the $C_4$ acetylenes, where the extractive solvent is separated from the crude isoprene product and the $C_4$ acetylenes. In some embodiments, the degassing zone can further include an acetylene washer column coupled to the degasser column to remove the extractive solvent from the crude isoprene product and the $C_4$ acetylenes.

In certain embodiments the system can further include a selective hydrogenation reactor for the $C_4$ acetylenes in the $C_4$ stream allocated upstream of the butadiene extraction plant to convert acetylenes to butadiene and 1-butene. Such a technology is already available commercially and provided by companies such as BASF, UOP and KBR.

In certain embodiments, the system can further include a dimerization heat exchanger coupled to the $C_5$ purification column to dimerize cyclopentadiene present in the $C_5$ hydrocarbon mixture to dicyclopentadiene. The system can also include a further hydrogenation reactor for converting the remaining undimerized cyclopentadiene to cyclopentene and cyclopentane.

The heavy ends ($C_5$+) hydrocarbons can include, e.g., dicyclopentadiene piperidine, cyclopentane, hexane, 1-hexene, 1,2-hexadiene, methyl-cyclopentadiene, benzene and cyclohexene. The light ends of the $C_5$ hydrocarbon mixture can include, e.g., pentane and isomers thereof, isoprene, pentadiene and isomers thereof, pentene and isomers thereof, and cyclopentene.

The system can further include a $C_5$ washer column that is coupled to the downstream of the $C_5$ purification column. The $C_5$ washer column can receive the light ends of the $C_5$ hydrocarbon mixture from the $C_5$ purification column and an extractive solvent, where the extractive solvent absorbs isoprene from the $C_5$ hydrocarbon mixture. The extractive solvent can include an aqueous solution of n-methyl 2-pyrrolidone having about 91.7% by weight of n-methyl 2-pyrrolidone and about 8.3% by weight of water. The $C_5$ washer column can generate an overhead product including $C_5$ components that are not absorbed by the extractive solvent. The overhead product of the $C_5$ washer column can include $C_5$ alkanes (including pentane and isopentane), paraffins and $C_5$ mono-olefins (including pentene and isomers thereof). The $C_5$ washer column can generate a bottom product including the extractive solvent, acetylenes, and $C_5$ di-olefins, which can include pentadienes. The $C_5$ washer column can generate a side product including isoprene. In certain embodiments, the side product of the $C_5$ washer column can further include $C_5$ mono-olefins and di-olefins impurities.

The system can further include an absorption column that is coupled to the downstream of the $C_5$ washer column. The $C_5$ washer column can receive an extractive solvent and the side product of the $C_5$ washer column, where isoprene along with $C_5$ mono-olefins is separated from $C_5$ di-olefins with the aid of the extractive solvent in the absorption column. The extractive solvent can include an aqueous solution of n-methyl 2-pyrrolidone having about 91.7% by weight of n-methyl 2-pyrrolidone and about 8.3% by weight of water. The absorption column can generate an overhead product including isoprene and $C_5$ mono-olefins, which can include cyclopentene and pentene isomers. The absorption column can generate a bottom product including $C_5$ diolefins.

The system can further include a distillation column that is coupled to the downstream of the absorption column. The distillation column can receive the overhead product of the absorption column, where isoprene is distilled from the overhead product of the absorption column.

In accordance with another embodiment of the presently disclosed subject matter, processes for separating and purifying butadiene and isoprene from a $C_4$ hydrocarbon mixture including butadiene and a $C_5$ hydrocarbon mixture including isoprene are provided. The processes include feeding a $C_5$ hydrocarbon mixture including isoprene to a $C_5$ purification column and separating the light ends of the $C_5$ hydrocarbon mixture from the heavy ends ($C_5$+) hydrocarbons in the $C_5$ purification column. The processes can also include feeding the light ends of the $C_5$ hydrocarbon mixture, a $C_4$ hydrocarbon mixture including butadiene, and an extractive solvent to a mainwasher column and co-extracting isoprene from the light ends of the $C_5$ hydrocarbon mixture and butadiene from the $C_4$ hydrocarbon mixture by using the extractive solvent in the mainwasher column to provide a crude butadiene product, $C_4$ acetylenes, and a crude isoprene product. The extractive solvent can be an aqueous solution of n-methyl 2-pyrrolidone having about 91.7% by weight of n-methyl 2-pyrrolidone and about 8.3% by weight of water.

The processes can further include feeding the crude butadiene product, the crude isoprene product, the extractive solvent, and the $C_4$ acetylenes to a rectifier column and separating the crude butadiene product from the crude isoprene product, the extractive solvent and the $C_4$ acetylenes in the rectifier column. In some embodiments, $C_5$ impurities leave the rectifier column with the crude butadiene product. The $C_5$ impurities can include 1-pentene. Furthermore, the processes can include removing acetylene traces present in the crude butadiene product by using a solvent in an afterwasher column. In some embodiments, the crude butadiene product recovered from the afterwasher column includes propyne. Thus, the process can include removing propyne from the crude butadiene product in a propyne column. Furthermore, the processes include feeding the crude butadiene product to a butadiene finishing column and purifying 1,3-butadiene from the crude butadiene product in the butadiene finishing column. In some embodiments, the 1,3-butadiene purified from the butadiene finishing column can have a purity of at least about 99.6% by weight.

In addition, the processes include feeding the crude isoprene product, the extractive solvent and the $C_4$ acetylenes to a degasser column, and separating the extractive solvent from the crude isoprene product and the $C_4$ acetylenes in the degasser column. The processes can also include removing the extractive solvent from the crude isoprene product and the $C_4$ acetylenes in an acetylene washer column. The processes further include feeding the crude isoprene product and the $C_4$ acetylenes to an isoprene finishing column and purifying isoprene from the crude isoprene product and the $C_4$ acetylenes in the isoprene finishing column. The process can include operating the isoprene finishing column at a vacuum of about 50 kiloPascals (kPa) (0.5 atmosphere). In some embodiments, the isoprene purified from the isoprene finishing column has a purity of about 98.6% to about 99.6% by weight.

The processes can further include removing cyclopentadiene present in the $C_5$ hydrocarbon mixture by dimerizing cyclopentadiene to dicyclopentadiene in a dimerization heat exchanger. This can be followed by a selective hydrogenation reaction of the unconverted cyclopentadiene to cyclopentene and cyclopentane.

The process can further include feeding the light ends of the $C_5$ hydrocarbon mixture from the $C_5$ purification column and an extractive solvent to a $C_5$ washer column, where isoprene can be separated from the $C_5$ hydrocarbon mixture by the extractive solvent to generate an overhead product including $C_5$ components that are not absorbed by the extractive solvent, a bottom product including the extractive solvent, $C_5$ di-olefins, and acetylenes, and a side product including isoprene. The side product of the $C_5$ washer column can include $C_5$ mono-olefins and di-olefins impurities. The process can further include feeding the side product of the $C_5$ washer column to an absorption column, where isoprene along with $C_5$ mono-olefins can be separated from $C_5$ di-olefins with the aid of an extractive solvent to generate an overhead product including isoprene and $C_5$ mono-olefins and a bottom product including $C_5$ diolefins and the extractive solvent including the solvent fed to the $C_5$ washer column. The process can further include feeding the overhead product of the absorption column to a distillation column, where isoprene can be distilled from the overhead product of the absorption column.

DETAILED DESCRIPTION

The presently disclosed subject matter provides co-extracting systems and processes for separating and purifying butadiene and isoprene from a $C_4$ hydrocarbon mixture including butadiene and a $C_5$ hydrocarbon mixture including isoprene.

The term "about" or "substantially" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

As used herein, the term "co-extracting," "co-extraction," or "co-extracted" means extracting or extraction of at least two materials or compounds in one process or in one extractive distillation column. For example, the presently disclosed subject matter provides a co-extraction system for butadiene and isoprene, where butadiene and isoprene are extracted in one extractive distillation column, e.g., a mainwasher column.

While technologies for separating and purifying butadiene or isoprene from a $C_4$ or $C_5$ hydrocarbon mixture are known in the art, at least two extraction plants or systems are required to extract both butadiene and isoprene. It is not known in the art to co-extract butadiene and isoprene in one system. The presently disclosed systems and processes can co-extract butadiene and isoprene. Moreover, the extracted butadiene and isoprene have a high purity, e.g., at least about 99.6% by weight, or about 98.6% to about 99.6% by weight.

Figure 1:
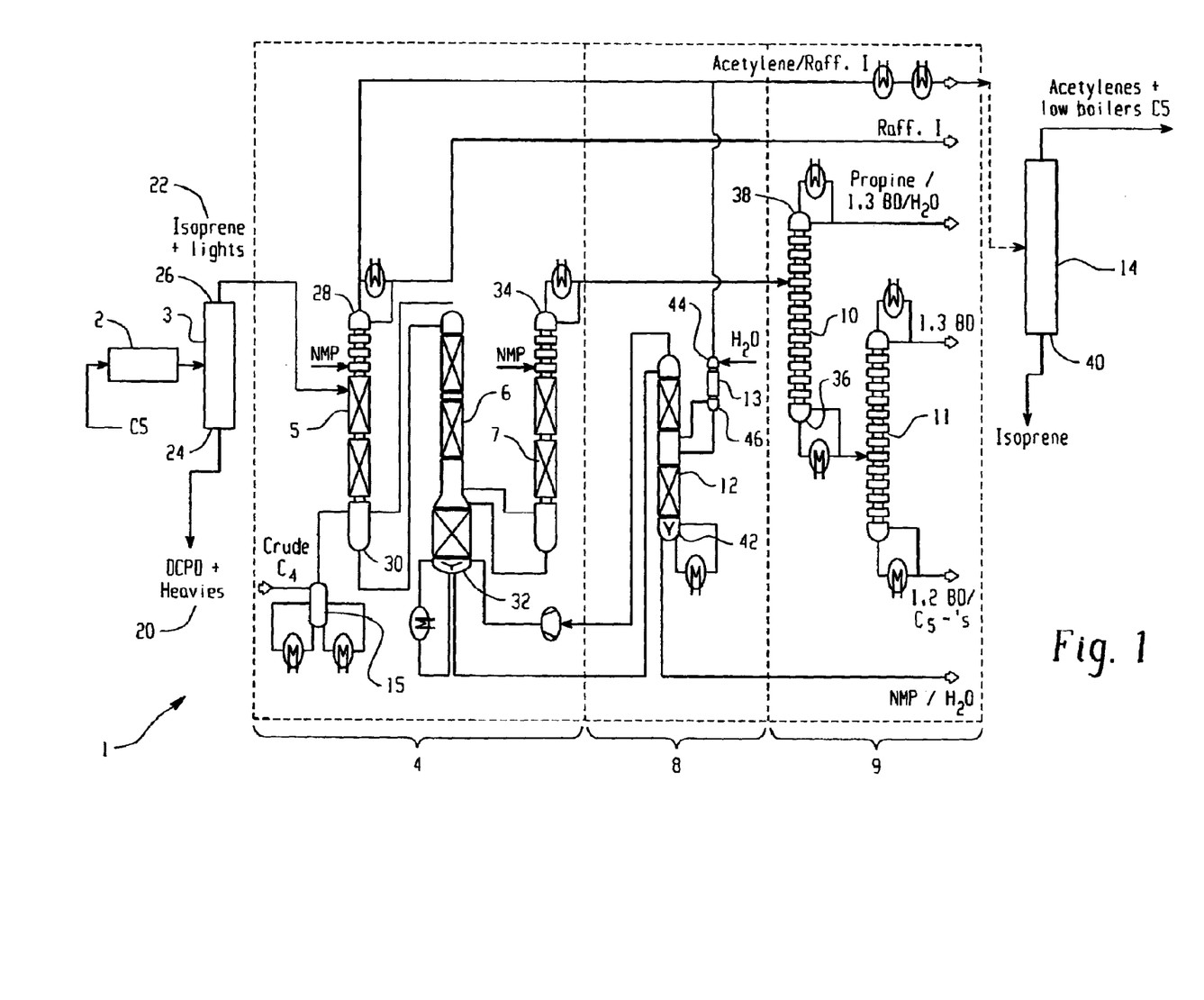
FIG. 1 shows a co-extraction system for separating and purifying butadiene and isoprene in accordance with one non-limiting exemplary embodiment of the disclosed subject matter.
Figure 2:
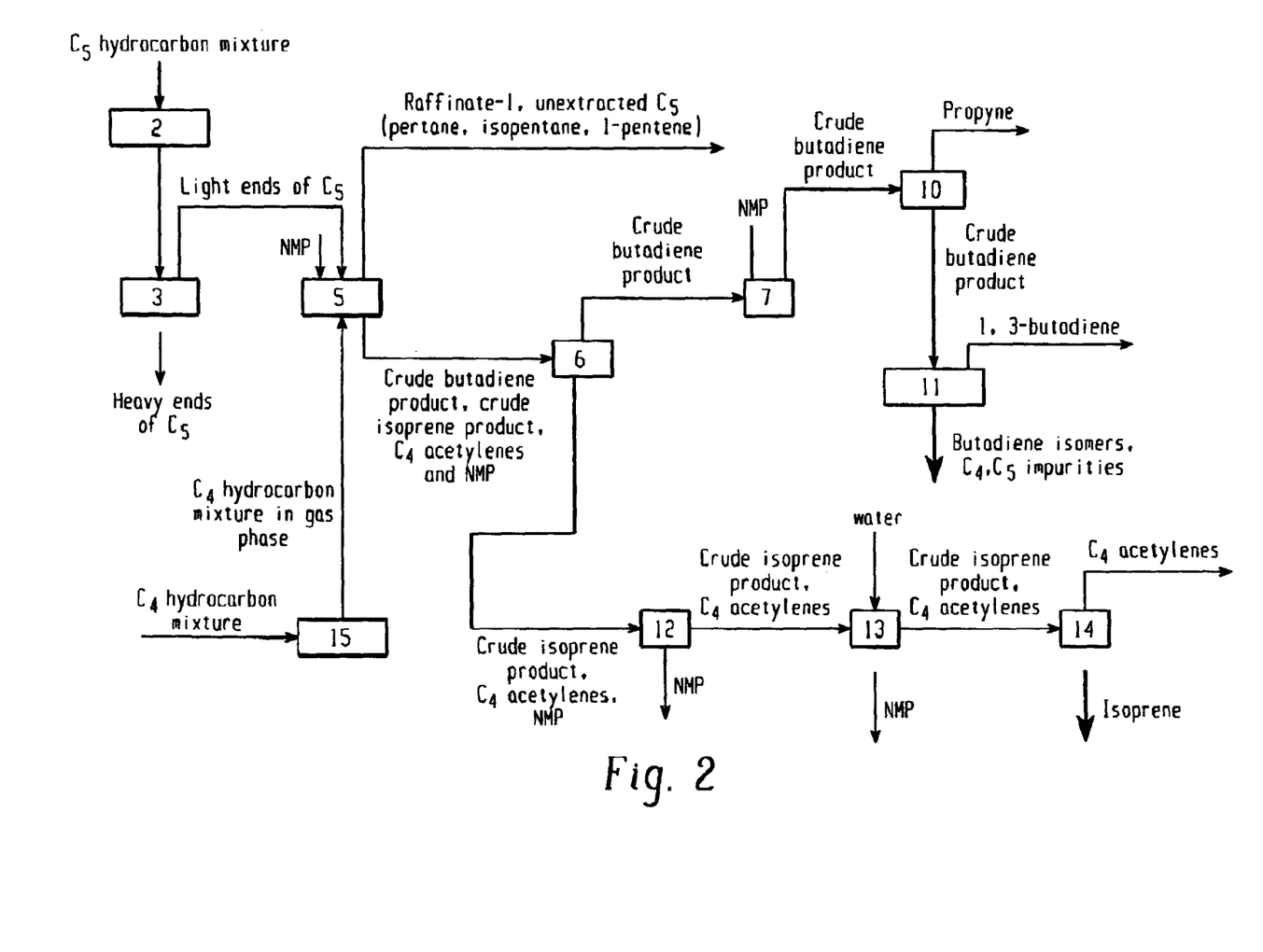
FIG. 2 shows a process for separating and purifying butadiene and isoprene in accordance with one non-limiting exemplary embodiment of the disclosed subject matter.

For the purpose of illustration and not limitation, FIG. 1 shows a co-extraction system 1 in accordance with one embodiment of the disclosed subject matter. FIG. 2 shows a co-extracting process in accordance with one embodiment of the disclosed subject matter. As shown in FIG. 1, the co-extraction system 1 includes a heat treatment/hydrogenation reactor 2. As shown in FIGS. 1 and 2, a $C_5$ hydrocarbon mixture including isoprene is fed to the heat treatment/hydrogenation reactor 2. A $C_5$ hydrocarbon mixture can include isoprene, trans- and cis-1,3-pentadiene, cyclopentadiene (DCPD) as conjugated diolefins, together with pentanes, n-pentenes, isoamylene, cyclopentene, higher acetylenes, methyl pentane isomers, piperylene isomers and methyl cyclobutane. A thermal dimerization is carried out and cyclopentadiene present in the $C_5$ hydrocarbon mixture is dimerized to form di-cyclopentadiene in the heat treatment/hydrogenation reactor 2. The dimerization reaction can be conducted at a temperature of about 90° C. to about 130° C. using medium pressure steam and a pressure of about 100 kPa to about 900 kPa (about 1 barg to about 9 barg). The $C_5$ hydrocarbon mixture is heated in the dimerization heat exchanger for about 5 to about 200 minutes. A substantial amount of cyclopentadiene, e.g., at least about 92% by weight, is removed in this process. Optionally, a further selective hydrogenation can follow to convert any remaining cyclopentadiene to cyclopentene and cyclopentane as discussed in, for example, U.S. Pat. Nos. 3,439,060 and 4,471, 153. Therefore all cyclopentadiene present in $C_5$ stream can be converted to dicyclopentadiene, cyclopentene and cyclopentane. Optionally, the hydrogenation reactor 2 can be placed after the $C_5$ purification column.

Example processes for removing cyclopentadiene present in a $C_5$ hydrocarbon mixture by thermal dimerization are disclosed, for example, in U.S. Pat. Nos. 2,768,224, 2,971, 036, and 3,692,861. In order to obtain very pure isoprene that is suitable for polymerization to polyisoprene, it can be important to remove cyclopentadiene from a $C_5$ hydrocarbon mixture because cyclopentadiene has a poisoning effect upon the so-called Ziegler-type catalyst and retards polymerization. In addition, cyclopentadiene can clog downstream columns or boilers in the extractive distillation zone if it dimerizes to dicyclopentadiene. The $C_5$ hydrocarbon mixture can be obtained by thermal cracking of a petroleum fraction, e.g., Liquefied Petroleum Gases ("LPG"), naphtha and the like.

As shown in FIGS. 1 and 2, the $C_5$ hydrocarbon mixture is then fed to a $C_5$ purification column 3, where the heavy ends ($C_5$+) hydrocarbons 20 and the light ends of the $C_5$ hydrocarbon mixture 22 are separated. For example, the heavy ends ($C_5$+) hydrocarbons 20 leave from a bottom 24, and the light ends of the $C_5$ hydrocarbon mixture leave from an overhead or top 26, of the $C_5$ purification column 3. Heavy ends ($C_5$+) hydrocarbons include dicyclopentadiene, piperidine, cyclopentane, hexane, 1-hexene, 1,2-hexadiene, methyl-cyclopentadiene, benzene and cyclohexene. Certain $C_5$ hydrocarbons, e.g., piperidine and cyclopentane, can be separated with hydrocarbons having 6 or more carbon atoms from isoprene, because their boiling points are higher than isoprene's. Light ends of a $C_5$ hydrocarbon mixture include pentane and isomers thereof, isoprene, pentene (e.g., 1-pentene) and isomers thereof, pentane and isomers thereof (e.g., isopentane), pentadiene and isomers thereof, and cyclopentene.

As shown in FIGS. 1 and 2, the light ends of the $C_5$ hydrocarbon mixture including isoprene enter an extraction zone 4. The extraction zone 4 can include a mainwasher column 5 and a rectifier column 6. The light ends of the $C_5$ hydrocarbon mixture including isoprene enter the mainwasher column from its top 28. In the $C_4$, stream an optional selective hydrogenation reactor for $C_4$ acetylene can be installed upstream to convert these components to butadiene and 1-butenes using commercially available technologies. A $C_4$ hydrocarbon mixture including butadiene enters the mainwasher column 5 from its bottom 30. The $C_4$ hydrocarbon mixture can be obtained by thermal cracking of a petroleum fraction, e.g., LPG, naphtha and the like. A $C_4$ hydrocarbon mixture can include butanes, 1-butene, isobutene, vinylacetylene, ethylacetylene and 1,2-butadiene, 1,3-butadiene, isobutane, trans-2-butene, cis-2-butene, 1-butyne, and small amounts of $C_3$ hydrocarbons, such as propane, propyne and propadiene, and/or $C_5$ hydrocarbons such as isopentane. In the mainwasher column 5, butadiene and isoprene are co-extracted from the $C_4$ hydrocarbon mixture and the $C_5$ hydrocarbon mixture, respectively, with the aid of an extractive solvent, thereby generating a crude butadiene product and a crude isoprene produce. Acetylenes (e.g., vinylacetylene and ethylacetylene) are also extracted from the $C_4$ hydrocarbon mixture in the mainwasher column 5 by the extractive solvent, and are referred to as "$C_4$ acetylenes."

The extractive solvent can be conventional solvents, e.g., N-alkyl-substituted cyclic aliphatic acid amides (lactams) having 5 ring members, e.g., N-alkylpyrrolidones (e.g., n-methyl 2-pyrrolidone ("NMP")), acetonitrile, dimethylformamide, acetone, furfural, butyrolactone, furfuraldehyde, methoxypropionitrile, N-alkyl-substituted lower aliphatic acid amides, e.g., dimethylformamide, diethylformamide, dimethylacetamide, diethylacetamide and formylmorpholine. In one embodiment, the extractive solvent is NMP or an aqueous solution of NMP. NMP, especially an aqueous NMP solution, can be superior to other conventional solvents, because it is non-toxic, non-carcinogenic, and can be treated by conventional biological waste water treatment. In addition, an aqueous NMP solution is non-corrosive, thereby allowing the use of carbon steel as construction material without the need for a corrosion inhibitor. NMP also has low solvent losses due to its resistance to hydrolysis and thermal decomposition as well as its high boiling point, and thus, there will be no vapor losses. Furthermore, NMP is less expensive than other extractive solvents. An aqueous solution of NMP can contain up to 15% by weight of water. In one embodiment, the extractive solution is an aqueous solution of NMP including about 91.7% by weight of NMP and about 8.3% by weight of water.

In some embodiments, the extraction zone 4 includes a flash vessel 15, as shown in FIG. 1. The $C_4$ hydrocarbon mixture can be vaporized in the flash vessel 15 before entering the mainwasher column 5, as shown in FIGS. 1 and 2. The $C_4$ hydrocarbon mixture in gas phase is passed through the mainwasher column 5 counter-currently to the aqueous NMP solution. For extracting 1,3-butadiene from a $C_4$ hydrocarbon mixture, NMP can act as an absorbent over various absorption and desorption stages. For example, 1,3-butadiene is absorbed by NMP while the butenes and butanes present in a $C_4$ hydrocarbon mixture remain in the gas phase. As such, 1,3-butadiene is separated from butenes and butanes. The overhead product of the mainwasher column 5 includes butenes and butanes and is designated as Raffinate-1. The flow rate of the aqueous NMP solution can be adjusted to minimize the amount of 1,3-butadiene in the overhead product (e.g., Raffinate-1) of the mainwasher column 5, e.g., about 0.1% to about 0.2% by weight of 1,3-butadiene in the overhead product. A crude butadiene product, the extractive solvent (e.g., NMP), and $C_4$ acetylenes (e.g., vinylacetylene and ethylacetylene) leave the mainwasher column 5 from its bottom 30. The crude butadiene product includes 1,3-butadiene and its isomers, e.g., 1,2-butadiene. In some embodiments, the crude butadiene product may include small amounts of $C_4$ impurities, e.g., cis-2-butene and trans-2-butene. Processes and technologies for using NMP to extract butadiene from a $C_4$ hydrocarbon mixture are disclosed, e.g., in U.S. Pat. Nos. 4,310,388, and 6,337,429, and German Patent Publication No. DE 2724365, each of which is hereby incorporated by reference in its entirety.

For extracting isoprene from a $C_5$ hydrocarbon mixture, the light ends of the $C_5$ hydrocarbon mixture in liquid phase with a temperature close to that of the extractive solvent (e.g., aqueous NMP solution) enters the mainwasher column 5 from its top 28, as shown in FIG. 2. The light ends of the $C_5$ hydrocarbon mixture are passed through the mainwasher column 5 co-currently to the aqueous NMP solution. Isoprene is extracted from the light ends of $C_5$ hydrocarbon mixture by the extractive solvent (e.g., aqueous NMP solution). A crude isoprene product including isoprene leaves the mainwasher column 5 from its bottom 30. In some embodiments, the crude isoprene product may include a small amount of $C_5$ impurities, e.g., 1-pentene. The $C_5$ hydrocarbons that are not extracted by the extractive solvent, including mainly pentane, isopentane and partly 1-pentene, are stripped from the mainwasher column 5 by the rising vapors of the $C_4$ hydrocarbon mixture. The unextracted $C_5$ hydrocarbons leave the mainwasher column 5 from its top as part of the overhead product of the mainwasher column 5. The flow rate of the aqueous NMP solution can be adjusted to minimize the amount of isoprene in the overhead product of the mainwasher column 5, e.g., about 0.2% to 0.6% by weight of isoprene in the overhead product.

The crude isoprene product, the crude butadiene product, the extractive solvent and $C_4$ acetylenes leave from the bottom 30 of the mainwasher column 5, and enter a rectifier column 6, as shown in FIGS. 1 and 2. In the rectifier column 6, the crude butadiene product is separated from the crude isoprene product, the extractive solvent, and the $C_4$ acetylenes. The crude butadiene product leaves the rectifier column 6 in gas phase as a side draw stream. Most of the $C_5$ impurities (e.g., 1-pentene) leave the rectifier column 6 with the crude butadiene product. The $C_4$ acetylenes, the crude isoprene product and the extractive solvent, with or without traces of $C_5$ impurities (e.g., 1-pentene) leave the rectifier column 6 from its bottom 32 and enter a degassing zone 8, as shown in FIGS. 1 and 2. Therefore, the crude butadiene product and the crude isoprene product are separated in the rectifier column 6.

The extraction zone 4 can further include an afterwasher column 7. After leaving the rectifier column 6, the crude butadiene product in gas phase can be fed to an afterwasher column 7 to remove acetylene traces that may escape with the crude butadiene product in the side draw stream from the rectifier column 6 by a fresh aqueous NMP solution having about 91.7% of NMP and about 8.3% of water. The fresh aqueous NMP solution can be fed to a top 34 of the afterwasher column 7. The crude butadiene product is recovered in the overhead product of the afterwasher column 7. In some embodiments, the overhead product of the afterwasher column 7 includes propyne that is an impurity present in a $C_4$ hydrocarbon mixture. NMP solvent is not present in the overhead due to its high boiling point.

The crude butadiene product enters a distillation zone 9 for further purification. In certain embodiments, the distillation zone 9 includes a propyne column 10. In the propyne column 10, propyne and the crude butadiene product are separated. Propyne is removed as overhead from the propyne column 10 and the crude butadiene product leaves the propyne column 10 from its bottom 36 and enters a butadiene finishing column 11, as shown in FIGS. 1 and 2. In the butadiene finishing column 11, 1,3-butadiene is withdrawn from a top 38 of the column 11 and butadiene isomers (e.g., 1,2-butadiene) as well as other $C_4$ impurities (e.g., trans-2-butene and cis-2-butene) are rejected in the bottom of the column 36. In some embodiments, small amounts of $C_5$ impurities (mainly 1-pentene) and traces of isoprene are rejected in a bottom 40 of an isoprene finishing column 14. A highly pure 1,3-butadiene can be produced in the butadiene finishing column 11. In some embodiments, the purified 1,3-butadiene has a purity of at least 99% by weight, e.g., at least about 99.6% by weight.

The $C_4$ acetylenes, the crude isoprene product and the extractive solvent, with or without traces of $C_5$ impurities (e.g., 1-pentene) leave the rectifier column 6 from its bottom and enter a degassing zone 8, as shown in FIGS. 1 and 2. The degassing zone 8 can include a degasser column 12. The extractive solvent is separated from the crude isoprene product and $C_4$ acetylenes in the degasser column 12. The extractive solvent leaves the degasser column 12 from its bottom 42. The extractive solvent can be recycled to the extraction zone 4. The crude isoprene product reduces polymerization of acetylene by diluting the concentration of acetylene in the degasser column 12, which is operated at a higher temperature than other columns in certain embodiments. In certain embodiments, the degassing zone 8 can include an acetylene washer column 13, as shown in FIGS. 1 and 2. The crude isoprene product and $C_4$ acetylenes, with or without traces of $C_5$ impurities (e.g., 1-pentene), leave the degasser column 12 as a side draw stream in gas phase and enter an acetylene washer column 13, as shown in FIGS. 1 and 2. The acetylene washer column 13 further removes any extractive solvent, which may escape with the crude isoprene and $C_4$ acetylenes from the degasser column 12. In one example, water is added to a top 44 of the acetylene washer column 13 to absorb the extractive solvent into a liquid phase, which is withdrawn from a bottom 46 of the column 13. The crude isoprene product and $C_4$ acetylenes, with or without traces of $C_5$ impurities (e.g., 1-pentene), are dewatered in successive settling vessels, and are fed to an isoprene finishing column 14, as shown in FIGS. 1 and 2. In the isoprene finishing column 14, isoprene is separated from $C_4$ acetylenes and $C_5$ impurities (e.g., 1-pentene). $C_4$ acetylenes and $C_5$ impurities leave as the overhead product of the isoprene finishing column 14. $C_4$ acetylenes can be hydrogenated and used as fuel gas or as cracker feed, or burned in a flare system. Isoprene is withdrawn from the bottom 40 of the isoprene finishing column 14. A highly pure isoprene is produced in the isoprene finishing column 14. In some embodiments, the purified isoprene has a purity of about 98.6% to 99.6% by weight. The isoprene finishing column 14 can be operated under a vacuum of about 0.5 atmosphere to avoid polymerization of acetylenes and isoprene.

In some embodiments, the system can include an isoprene polishing column (not shown) to obtain a higher purified isoprene, e.g., isoprene with a purity of greater than 99.6% by weight. Isoprene can be separated from other heavy hydrocarbons (e.g., dimerized dienes such as traces of dicyclopentadiene and venylcyclohexene) in the isoprene polishing column. The isoprene polishing column can be operated under the same vacuum as that for the isoprene finishing column.

Figure 3:
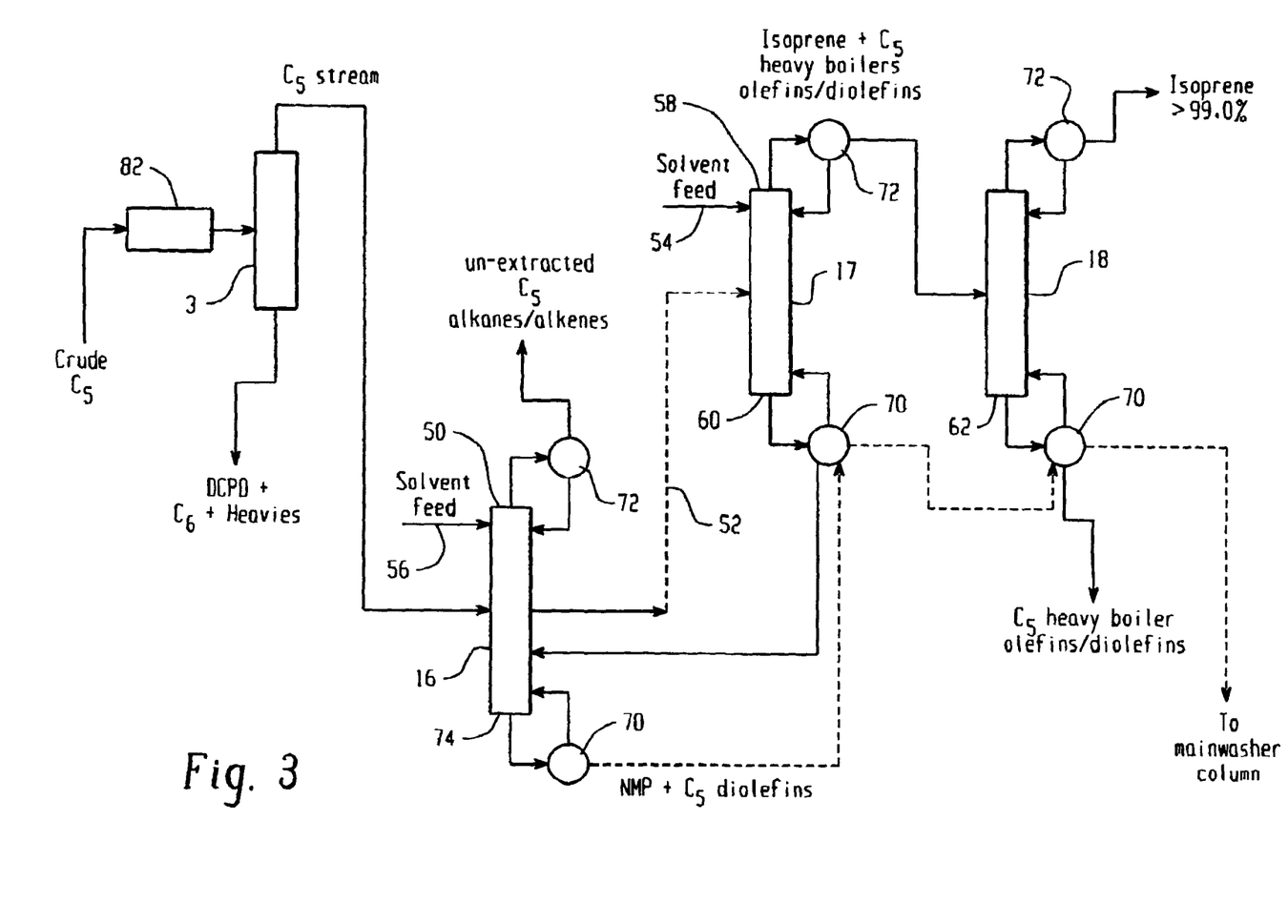
FIG. 3 shows a co-extraction system for separating and purifying butadiene and isoprene in accordance with one non-limiting exemplary embodiment of the disclosed subject matter.
Figure 4:
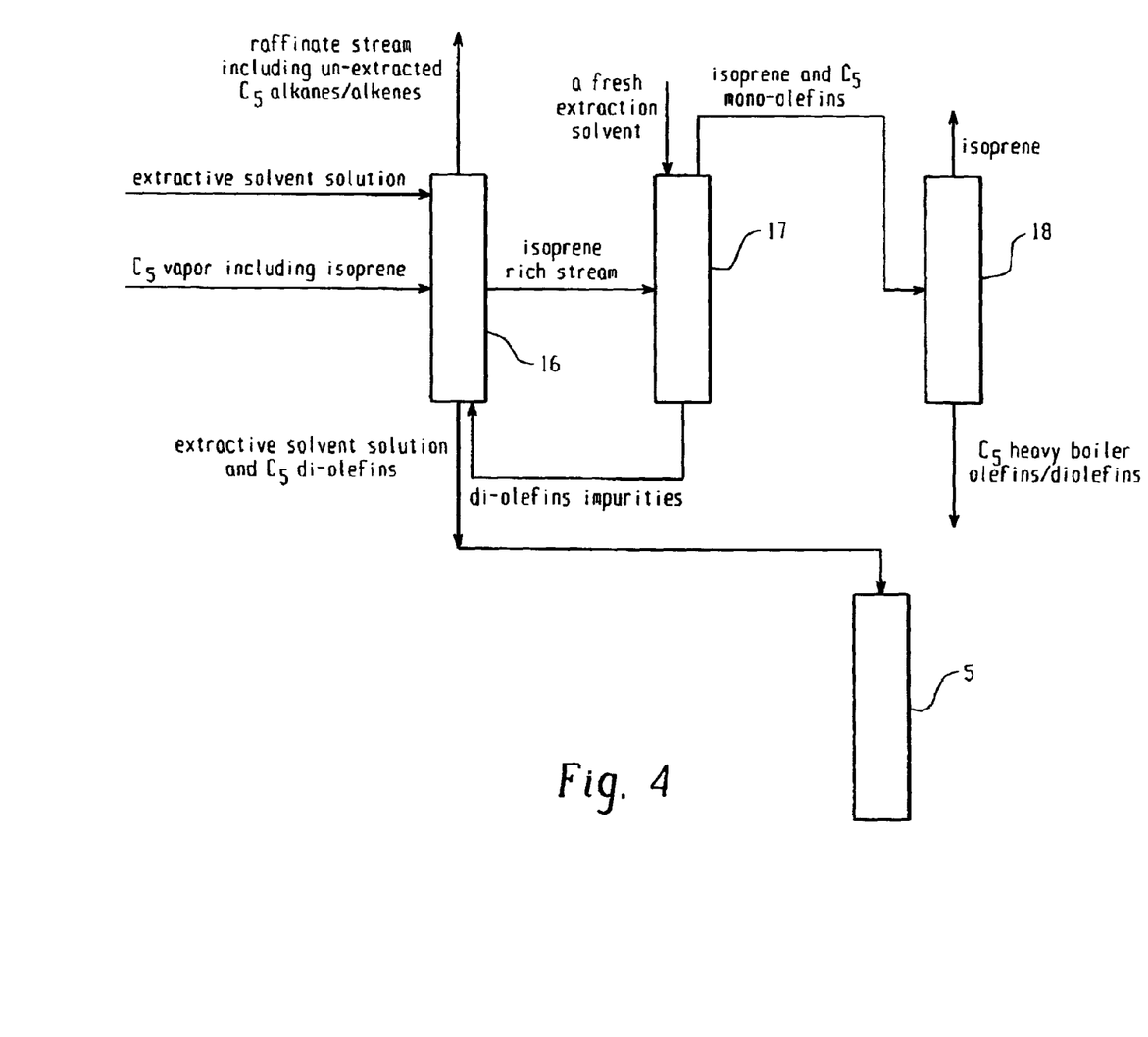
FIG. 4 shows a process for separating and purifying butadiene and isoprene in accordance with one non-limiting exemplary embodiment of the disclosed subject matter.

Additionally or alternatively, the system can include a $C_5$ washer column 16. For the purpose of illustration and not limitation, FIGS. 3 and 4 show an exemplary system and a process in accordance with another embodiment of the disclosed subject matter, respectively. As shown in FIGS. 3 and 4, crude $C_5$ can enter a heat exchanger/hydrogenation reactor 82 and exit as a $C_5$ hydrocarbon and enter a $C_5$ purification column 3 with the light ends of the $C_5$ hydrocarbon mixture including isoprene produced or separated from the $C_5$ purification column 3 as shown in FIGS. 1 and 2 can enter a $C_5$ washer column 16 at about the middle of the column as vapor. An extractive solvent 56 can be introduced to a top 50 of the $C_5$ washer column 16 as liquid to absorb the isoprene from the $C_5$ vapors. The extractive solvent can include an aqueous solution of n-methyl 2-pyrrolidone having about 91.7% by weight of n-methyl 2-pyrrolidone and about 8.3% by weight of water.

As shown in FIG. 3, the $C_5$ washer column 16 can be fitted with a condenser and a reboiler. The overhead from the $C_5$ washer column can be raffinate stream that includes $C_5$ components that are not absorbed by the extractive solvent, including alkanes (e.g., pentane, isopentane), paraffins and mono-olefins (e.g., pentene (e.g., 1-penetene) and isomers thereof). The bottom product of the $C_5$ washer column can include the extractive solvent along with di-olefins (e.g., pentadienes) and certain acetylenes. An isoprene rich stream 52 can be taken out of the side of the $C_5$ washer column 16 at a location below the middle of the $C_5$ washer column 16 by a vapor draw off stream.

The vapor draw of isoprene can enter an absorption column (17 in FIGS. 3 and 4) close to the bottom tray, and a fresh feed of NMP 54 can be introduced to a top 56 of the column 17. The absorption column 17 can be fitted with a reboiler 70 and a condenser 72. In the absorption column 17, isoprene along with certain mono-olefins such as cyclopentene and certain pentene isomers can be separated from impurities of di-olefins carried in the vapor phase with the isoprene by the fresh solvent fed from the top 58 of this column 17. This extract that includes diolefins and extractive solvent can leave the bottom 60 of the absorption column 17 and can be returned back to the $C_5$ washer column 16. The isoprene along with the remaining $C_5$ hydrocarbon mixture can be withdrawn from the overhead of the absorption column 17 and can enter a distillation column (18 in FIGS. 3 and 4). In the distillation column 18, isoprene can be separated out as the light component from the remaining $C_5$ components, which are heavier than isoprene and can leave the distillation column 18 from its bottom 62. This stream can be remixed with the Pygas aromatic stream of $C_6+$. The purity of the isoprene overhead product can be about 99 wt % or more, e.g., in a range of from about 99.0 wt % to about 99.9 wt %. The column 18 overhead pressure is close to atmospheric and is preferably about 20 kPa to about 100 kPa (about 0.2 barg to about 1 barg).

The bottom stream 74 from the $C_5$ washer column 16 at about 160° C. can be used to heat the boilers 70 of the absorption column 17 and the distillation column 18, and can be used to heat up the propyne column boiler downstream of the butadiene plant, which can save separation energy and ensure heat integration in the butadiene plant. After releasing its heat, the bottom stream 74 from the $C_5$ washer column 16 can then be further cooled to about 38° C. to about 45° C. and can be combined with the extractive solvent stream that is recycled from the butadiene plant and can enter the mainwasher column 5 from the top 28.

$C_4$ impurities can be separated from $C_5$ di-olefins components based on their selectivity in the extractive solvent. The $C_5$ components can enter the rectifier column. As shown in FIGS. 1 and 2, the crude isoprene product ($C_5$ components) along with the $C_4$ acetylenes can be carried in the extractive solvent to the degasser column. As shown in FIGS. 1 and 2, in the degasser column, the $C_4$ acetylenes and the crude isoprene product ($C_5$ components, which include primarily diolefins, e.g., pentadienes isomers) are drawn off as vapor stream out of the extractive solvent. The bottom product of the degasser column can include the extractive solvent that is free of hydrocarbons and can be recycled back as fresh extractive solvent feed. Part of the recycled extractive solvent feed can be used for extracting the $C_5$ hydrocarbon mixture as described above, and then can rejoin the other extractive solvent feed before it enters the mainwasher column 5 of the butadiene plant.

EXAMPLES

The following examples are merely illustrative of the presently disclosed subject matter and they should not be considered as limiting the scope of the presently disclosed subject matter in any way.

Example 1

A commercially available process simulation software tool (PRO-II) was used to construct an in-house model describing the process embodiments given in this disclosure. Process simulation software tools for chemicals processes are known to one of ordinary skill in the art. The in-house model constructed has been used successfully to simulate butadiene extraction process by using an aqueous NMP solution in one butadiene plant. The in-house model was used to simulate the process of co-extraction of butadiene and isoprene in the same plant as described above and as shown in FIGS. 1 and 2.

The in-house model was verified against butadiene extraction plant data where an isoprene spike in the $C_4$ hydrocarbon feed stream to a mainwasher column was measured at different locations around the plant. The results were compared with the model results as shown in Table 1 where isoprene percent level in butadiene plant was taken as 100 units of measure in the feed to the mainwasher column. The results show that the plant data and the results from the model prediction were fairly comparable. This finding consolidates the workable schemes of the embodiments given in the disclosure which are based on simulation model results.

TABLE 1

| Isoprene level in downstream units to isoprene in feed to a mainwasher column | | |
|---|---|---|
| Column | Plant data | Model prediction |
| Acetylene washer column overhead | 80% | 88.5% |
| Mainwasher column overhead | 8% | 6.4% |
| Afterwasher column overhead | 5.4% | 5.1% |

The results of certain selected streams with main components by using the simulation model are shown in Table 2.

TABLE 2

Stream Composition Wet Bases

| Components | C$_4$ hydrocarbon mixture fed to a mainwasher column (wt %) | C$_5$ hydrocarbon mixture fed to a mainwasher column (wt %) | Overhead product of a mainwasher column (wt %) | Overhead product of an afterwasher column (wt %) | Butadiene purified from a butadiene finishing column (wt %) | Isoprene purified from an isoprene finishing column (wt %) |
|---|---|---|---|---|---|---|
| propyne | 0.0316 | | | 0.0375 | | |
| propadiene | 3.6429E−03 | | | | | |
| butane | 5.8969 | | 11.6103 | | | |
| isobutane | 1.2072 | | 2.3768 | | | |
| 1-butene | 12.5472 | | 24.7040 | | | |
| isobutene | 14.7248 | 0.1829 | 29.0449 | | | |
| trans-2-butene | 6.8850 | | 13.5556 | | | |
| cis-2-butene | 3.2380 | | 6.2308 | 0.1282 | 0.0542 | |
| 1,3-butadiene | 53.7831 | | 0.2000 | 93.0610 | 99.8241 | |
| 1,2-butadiene | 0.1752 | | 0.2526 | 0.0821 | | |
| 1-butyne | 0.1323 | | | | | |
| vinylacetylene | 0.8051 | | | | | |
| pentane | | 24.9004 | 7.2805 | | | |
| isoprene | | 43.9165 | 0.5349 | 0.5766 | | 98.8350 |
| 1-pentene | | 26.5482 | 1.7506 | 5.3298 | | |
| isopentane | 0.5401 | 4.4479 | 2.3639 | | | |
| butadiene dimers | 0.0251 | | | | | 0.4521 |

Example 2

The simulation model used in Example 1 was applied to obtain results for the process as depicted shown in FIGS. 3 and 4 to simulate isoprene/butadiene co-extraction using an aqueous NMP. The results of certain selected streams with main components are shown in Table 3 below.

TABLE 3

Stream Composition

| Components | C$_5$ hydrocarbon mixture fed to a C$_5$ washer column (wt %) | Overhead product of a C$_5$ washer column (wt %) | Bottom product of C$_5$ washer column going to mainwasher column (wt %) | Feed to absorption 1 from vapor draw of C$_5$ washer column (wt %) | Isoprene purified from absorption column 2 overhead (wt %) |
|---|---|---|---|---|---|
| 1-butene | 2.4637 | 3.4453 | | | |
| isobutene | 0.6358 | 0.8891 | | | |
| trans-2-butene | 0.3576 | 0.5001 | | | |
| cis-2-butene | 0.3576 | 0.5001 | | | |
| 1,3-butadiene | 10.3318 | 14.4478 | 0.9713 | 1.8987 | |
| pentane | 36.7966 | 51.4557 | | | |
| isoprene | 15.8949 | 0.8335 | | 62.0872 | 99.9548 |
| 1-pentene | 2.4637 | 3.4451 | | | |
| isopentane | 16.2130 | 22.6720 | | | |
| neopentane | 0.1590 | 0.2223 | | | |
| Trans2-pentene | 0.3576 | 0.4998 | | 1.5838E−03 | 2.5183E−03 |
| Cis2-pentene | 0.3576 | 0.4999 | | 3.3610E−03 | 5.1660E−03 |
| 1,2-pentadiene | 4.7266 | 1.3125E−03 | | | |
| Cis-1,3-pentadiene | 2.5410 | 2.99865E−06 | 0.4582 | 5.7895 | |
| Trans1,3-pentadiene | 2.5419 | 2.6229E−06 | 0.4587 | 10.9696 | |
| cyclopentene | 3.8011 | 3.4060E−04 | | 16.6834 | |
| NMP | | | 90.0218 | | |
| Water | | | 8.0832 | | |

The systems and methods disclosed herein include at least the following embodiments:

Embodiment 1

A co-extraction system for separating and purifying butadiene and isoprene from a C$_4$ hydrocarbon mixture comprising butadiene and a C$_5$ hydrocarbon mixture comprising isoprene, comprising: (a) a C$_5$ purification column to receive a C$_5$ hydrocarbon mixture comprising isoprene and separate the light ends of the C$_5$ hydrocarbon mixture from the heavy ends (C$_5$+) hydrocarbons; (b) an extraction zone, comprising: (i) a mainwasher column to receive the light ends of the C$_5$ hydrocarbon mixture, a C$_4$ hydrocarbon mixture comprising butadiene, and an extractive solvent, wherein butadiene and isoprene are co-extracted from the C$_4$ and C$_5$ hydrocarbon mixtures by using the extractive solvent to provide a crude butadiene product, C$_4$ acetylenes, and a crude isoprene product; and (ii) a rectifier column to receive the crude butadiene product, the crude isoprene product, the extractive solvent, and the $C_4$ acetylenes, wherein the crude butadiene product is separated from the crude isoprene product, the extractive solvent, and the $C_4$ acetylenes; (c) a distillation zone, comprising a butadiene finishing column to receive the crude butadiene product, wherein 1,3-butadiene is purified from the crude butadiene product; (d) a degassing zone, comprising a degasser column to receive the crude isoprene product, the extractive solvent, and the $C_4$ acetylenes, wherein the extractive solvent is separated from the crude isoprene product and the $C_4$ acetylenes; and (e) an isoprene finishing column to receive the crude isoprene product and the $C_4$ acetylenes, wherein isoprene is purified from the crude isoprene product and the $C_4$ acetylenes.

Embodiment 2

The system of embodiment 1, wherein the extractive solvent comprises an aqueous solution of n-methyl 2-pyrrolidone having about 91.7% by weight of n-methyl 2-pyrrolidone and about 8.3% by weight of water.

Embodiment 3

The system of embodiment 1 or embodiment 2, further comprising a dimerization heat exchanger coupled to the $C_5$ purification column to dimerize cyclopentadiene present in the $C_5$ hydrocarbon mixture to dicyclopentadiene.

Embodiment 4

The system of any of embodiments 1 to 3, wherein the crude butadiene product comprises 1,3-butadiene, 1,2-butadiene, cis-2-butene, and trans-2-butene.

Embodiment 5

The system of embodiment 4, wherein 1,3-butadiene is present in a greater amount than 1,2-butadiene, cis-2-butene, and trans-2-butene.

Embodiment 6

The system of any of embodiments 1 to 5, wherein the crude isoprene product comprises isoprene and 1-pentene.

Embodiment 7

The system of embodiment 6, wherein isoprene is present in a greater amount than 1-pentene.

Embodiment 8

The system of any of embodiments 1 to 7, the extraction zone further comprises (iii) an afterwasher column coupled to the rectifier column to remove acetylene traces present in the crude butadiene product by using a solvent.

Embodiment 9

The system of embodiment 8, wherein the solvent is n-methyl 2-pyrrolidone.

Embodiment 10

The system of embodiment 8, wherein the crude butadiene product recovered from the afterwasher column comprises propyne.

Embodiment 11

The system of embodiment 8, wherein the distillation zone further comprises a propyne column coupled to the afterwasher column to separate propyne from the crude butadiene product.

Embodiment 12

The system of any of embodiments 1 to 11, wherein the degassing zone further comprises an acetylene washer column coupled to the degasser column to remove the extractive solvent from the crude isoprene product and the $C_4$ acetylenes.

Embodiment 13

The system of any of embodiments 1 to 12, wherein the heavy ends ($C_5$+) hydrocarbons comprise piperidine, cyclopentane, hexane, 1-hexene, 1,2-hexadiene, methyl-cyclopentadiene, benzene and cyclohexene.

Embodiment 14

The system of embodiment 13, wherein the heavy ends ($C_5$+) hydrocarbons comprise dicyclopentadiene.

Embodiment 15

The system of any of embodiments 1 to 14, wherein the light ends of the $C_5$ hydrocarbon mixture comprise pentane and isomers thereof, isoprene, pentene and isomers thereof, pentadiene and isomers thereof, and cyclopentene.

Embodiment 16

The system of any of embodiments 1 to 15, further comprising a $C_5$ washer column that is coupled to the downstream of the $C_5$ purification column and receives the light ends of the $C_5$ hydrocarbon mixture from the $C_5$ purification column and an extractive solvent, wherein the extractive solvent absorbs isoprene from the $C_5$ hydrocarbon mixture.

Embodiment 17

The system of embodiment 16, wherein the extractive solvent comprises an aqueous solution of n-methyl 2-pyrrolidone having about 91.7% by weight of n-methyl 2-pyrrolidone and about 8.3% by weight of water.

Embodiment 18

The system of embodiment 16, wherein the $C_5$ washer column generates an overhead product comprising $C_5$ components that are not absorbed by the extractive solvent.

Embodiment 19

The system of embodiment 18, wherein the overhead product of the $C_5$ washer column comprises $C_5$ alkanes, paraffins and $C_5$ mono-olefins.

Embodiment 20

The system of embodiment 19, wherein the $C_5$ mono-olefins comprises pentene and isomers thereof.

Embodiment 21

The system of embodiment 19, wherein the $C_5$ alkanes comprises pentane and isopentane.

Embodiment 22

The system of embodiment 16, wherein the $C_5$ washer column generates a bottom product comprising the extractive solvent, $C_5$ di-olefins, and acetylenes.

Embodiment 23

The system of embodiment 22, wherein the di-olefins comprises pentadienes.

Embodiment 24

The system of embodiment 16, wherein the $C_5$ washer column generates a side product comprising isoprene.

Embodiment 25

The system of embodiment 24, wherein the side product of the $C_5$ washer column further comprises $C_5$ mono-olefins and di-olefins impurities.

Embodiment 26

The system of embodiment 25, further comprising an absorption column that is coupled to the downstream of the $C_5$ washer column and receives an extractive solvent and the side product of the $C_5$ washer column, wherein isoprene along with $C_5$ mono-olefins is separated from $C_5$ di-olefins with the aid of the extractive solvent in the absorption column.

Embodiment 27

The system of embodiment 26, wherein the extractive solvent comprises an aqueous solution of n-methyl 2-pyrrolidone having about 91.7% by weight of n-methyl 2-pyrrolidone and about 8.3% by weight of water.

Embodiment 28

The system of embodiment 26, the absorption column generates an overhead product comprising isoprene and $C_5$ mono-olefins.

Embodiment 29

The system of embodiment 28, wherein the mono-olefins comprises cyclopentene and pentene isomers.

Embodiment 30

The system of embodiment 26, wherein the absorption column generates a bottom product comprising $C_5$ diolefins and the extractive solvent.

Embodiment 31

The system of embodiment 28, further comprising a distillation column that is coupled to the downstream of the absorption column and receives the overhead product of the absorption column, wherein isoprene is distilled from the overhead product of the absorption column.

Embodiment 32

A process for separating and purifying butadiene and isoprene from a $C_4$ hydrocarbon mixture comprising butadiene and a $C_5$ hydrocarbon mixture comprising isoprene, comprising: feeding a $C_5$ hydrocarbon mixture comprising isoprene to a $C_5$ purification column; separating the light ends of the $C_5$ hydrocarbon mixture from the heavy ends ($C_5$+) hydrocarbons in the $C_5$ purification column; feeding the light ends of the $C_5$ hydrocarbon mixture, a $C_4$ hydrocarbon mixture comprising butadiene, and an extractive solvent to a mainwasher column; co-extracting isoprene from the light ends of the $C_5$ hydrocarbon mixture and butadiene from the $C_4$ hydrocarbon mixture by using the extractive solvent in the mainwasher column to provide a crude butadiene product, $C_4$ acetylenes, and a crude isoprene product; feeding the crude butadiene product, the crude isoprene product, the extractive solvent, and the $C_4$ acetylenes to a rectifier column; separating the crude butadiene product from the crude isoprene product, the extractive solvent and $C_4$ acetylenes in the rectifier column; feeding the crude butadiene product to a butadiene finishing column; purifying 1,3-butadiene from the crude butadiene product in the butadiene finishing column; feeding the crude isoprene product, the extractive solvent and the $C_4$ acetylenes to a degasser column; separating the extractive solvent from the crude isoprene product and the $C_4$ acetylenes in the degasser column; feeding the crude isoprene product and the $C_4$ acetylenes to an isoprene finishing column; and purifying isoprene from the crude isoprene product and the $C_4$ acetylenes in the isoprene finishing column.

Embodiment 33

The process of embodiment 32, wherein the extractive solvent comprises an aqueous solution of n-methyl 2-pyrrolidone having about 91.7% by weight of n-methyl 2-pyrrolidone and about 8.3% by weight of water.

Embodiment 34

The process of embodiment 32 or embodiment 33, further comprising removing cyclopentadiene present in the $C_5$ hydrocarbon mixture by dimerizing cyclopentadiene to dicyclopentadiene in a dimerization heat exchanger.

Embodiment 35

The process of any of embodiments 32 to 34, further comprising removing cyclopentadiene present in the $C_5$ hydrocarbon mixture by selective hydrogenation of cyclopentadiene to cyclopentene and cyclopentane.

Embodiment 36

The process of any of embodiments 32 to 35, further comprising a $C_4$ selective hydrogenation reactor for acetylenes present in the $C_4$ stream upstream of the butadiene extraction plant.

Embodiment 37

The process of any of embodiments 32 to 36, further comprising removing acetylene traces present in the crude butadiene product by using a solvent in an afterwasher column.

Embodiment 38

The process of any of embodiments 32 to 37, further comprising separating propyne from the crude butadiene product in a propyne column.

Embodiment 39

The process of any of embodiments 32 to 38, further comprising removing the extractive solvent from the crude isoprene product and the $C_4$ acetylenes in an acetylene washer column.

Embodiment 40

The process of any of embodiments 32 to 39, wherein the 1,3-butadiene purified in the butadiene finishing column has a purity of at least about 99.6% by weight.

Embodiment 41

The process of any of embodiments 32 to 40, wherein the isoprene purified in the isoprene finishing column has a purity of about 98.6% to about 99.6% by weight.

Embodiment 42

The process of any of embodiments 32 to 42, comprising operating the isoprene finishing column at a vacuum of about 0.5 atmosphere.

Embodiment 43

The process of any of embodiments 32 to 42, further comprising feeding the light ends of the $C_5$ hydrocarbon mixture from the $C_5$ purification column and an extractive solvent to a $C_5$ washer column.

Embodiment 44

The process of embodiment 43, further comprising absorbing isoprene from the $C_5$ hydrocarbon mixture by the extractive solvent in the $C_5$ washer column to generate an overhead product comprising $C_5$ components that are not absorbed by the extractive solvent, a bottom product comprising the extractive solvent, $C_5$ di-olefins, and acetylenes, and a side product comprising isoprene.

Embodiment 45

The process of embodiment 43, wherein the side product of the $C_5$ washer column comprises $C_5$ mono-olefins and di-olefins impurities.

Embodiment 46

The process of embodiment 44, further comprising feeding the side product of the $C_5$ washer column and an extractive solvent to an absorption column.

Embodiment 47

The process of embodiment 46, further comprising separating isoprene along with $C_5$ mono-olefins from $C_5$ di-olefins with the aid of the extractive solvent in the absorption column to generate an overhead product comprising isoprene and $C_5$ mono-olefins and a bottom product comprising $C_5$ diolefins and extractive solvent.

Embodiment 48

The process of embodiment 47, further comprising feeding the overhead product of the absorption column to a distillation column.

Embodiment 49

The process of embodiment 48, further comprising distilling isoprene from the overhead product of the absorption column in the distillation column.

Although the presently disclosed subject matter and its advantages have been described in detail, it should be understood that various changes, substitutions and alterations can be made herein without departing from the spirit and scope of the presently disclosed subject matter as defined by the appended claims. Moreover, the scope of the presently disclosed subject matter is not intended to be limited to the particular embodiments of the process, machine, manufacture, and composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such modifications.

What is claimed is:

1. A co-extraction system for separating and purifying butadiene and isoprene from a $C_4$ hydrocarbon mixture comprising butadiene and a $C_5$ hydrocarbon mixture comprising isoprene, comprising:
   (a) a $C_5$ purification column to receive a $C_5$ hydrocarbon mixture comprising isoprene and separate the light ends of the $C_5$ hydrocarbon mixture from the heavy ends ($C_5$+) hydrocarbons;
   (b) an extraction zone, comprising:
   (i) a mainwasher column to receive the light ends of the $C_5$ hydrocarbon mixture, a $C_4$ hydrocarbon mixture comprising butadiene, and an extractive solvent, wherein butadiene and isoprene are co-extracted from the $C_4$ and $C_5$ hydrocarbon mixtures by using the extractive solvent to provide a crude butadiene product, $C_4$ acetylenes, and a crude isoprene product; and
   (ii) a rectifier column to receive the crude butadiene product, the crude isoprene product, the extractive solvent, and the $C_4$ acetylenes, wherein the crude butadiene product is separated from the crude isoprene product, the extractive solvent, and the $C_4$ acetylenes;
   (c) a distillation zone, comprising a butadiene finishing column to receive the crude butadiene product, wherein 1,3-butadiene is purified from the crude butadiene product;
   (d) a degassing zone, comprising a degasser column to receive the crude isoprene product, the extractive solvent, and the $C_4$ acetylenes, wherein the extractive solvent is separated from the crude isoprene product and the $C_4$ acetylenes; and (e) an isoprene finishing column to receive the crude isoprene product and the $C_4$ acetylenes, wherein isoprene is purified from the crude isoprene product and the $C_4$ acetylenes.

2. The system of claim 1, wherein the extractive solvent comprises an aqueous solution of n-methyl 2-pyrrolidone having about 91.7% by weight of n-methyl 2-pyrrolidone and about 8.3% by weight of water.

3. The system of claim 1, further comprising a dimerization heat exchanger coupled to the $C_5$ purification column to dimerize cyclopentadiene present in the $C_5$ hydrocarbon mixture to dicyclopentadiene.

4. The system of claim 1, wherein the crude butadiene product comprises 1,3-butadiene, 1,2-butadiene, cis-2-butene, and trans-2-butene and wherein the crude isoprene product comprises isoprene and 1-pentene.

5. The system of claim 1, the extraction zone further comprises (iii) an afterwasher column coupled to the rectifier column to remove acetylene traces present in the crude butadiene product by using a solvent.

6. The system of claim 1, wherein the degassing zone further comprises an acetylene washer column coupled to the degasser column to remove the extractive solvent from the crude isoprene product and the $C_4$ acetylenes.

7. The system of claim 1, wherein the heavy ends ($C_5$+) hydrocarbons comprise piperidine, cyclopentane, hexane, 1-hexene, 1,2-hexadiene, methyl-cyclopentadiene, benzene and cyclohexene and wherein the light ends of the $C_5$ hydrocarbon mixture comprise pentane and isomers thereof, isoprene, pentene and isomers thereof, pentadiene and isomers thereof, and cyclopentene.

8. The system of claim 1, further comprising a $C_5$ washer column that is coupled to the downstream of the $C_5$ purification column and receives the light ends of the $C_5$ hydrocarbon mixture from the $C_5$ purification column and an extractive solvent, wherein the extractive solvent absorbs isoprene from the $C_5$ hydrocarbon mixture.

9. The system of claim 8, wherein the $C_5$ washer column generates an overhead product comprising $C_5$ components that are not absorbed by the extractive solvent wherein the overhead product of the $C_5$ washer column comprises $C_5$ alkanes, paraffins and $C_5$ mono-olefins and wherein the $C_5$ washer column generates a bottom product comprising the extractive solvent, $C_5$ di-olefins, and acetylenes.

10. The system of claim 8, further comprising an absorption column that is coupled to the downstream of the $C_5$ washer column and receives an extractive solvent and the side product of the $C_5$ washer column, wherein isoprene along with $C_5$ mono-olefins is separated from $C_5$ di-olefins with the aid of the extractive solvent in the absorption column.

11. The system of claim 10, the absorption column generates an overhead product comprising isoprene and $C_5$ mono-olefins and wherein the $C_5$ washer column generates a bottom product comprising the extractive solvent, $C_5$ di-olefins, and acetylenes.

12. The system of claim 11, further comprising a distillation column that is coupled to the downstream of the absorption column and receives the overhead product of the absorption column, wherein isoprene is distilled from the overhead product of the absorption column.

13. A process for separating and purifying butadiene and isoprene from a $C_4$ hydrocarbon mixture comprising butadiene and a $C_5$ hydrocarbon mixture comprising isoprene, comprising:
feeding a $C_5$ hydrocarbon mixture comprising isoprene to a $C_5$ purification column;
separating the light ends of the $C_5$ hydrocarbon mixture from the heavy ends ($C_5$+) hydrocarbons in the $C_5$ purification column;
feeding the light ends of the $C_5$ hydrocarbon mixture, a $C_4$ hydrocarbon mixture comprising butadiene, and an extractive solvent to a mainwasher column;
co-extracting isoprene from the light ends of the $C_5$ hydrocarbon mixture and butadiene from the $C_4$ hydrocarbon mixture by using the extractive solvent in the mainwasher column to provide a crude butadiene product, $C_4$ acetylenes, and a crude isoprene product;
feeding the crude butadiene product, the crude isoprene product, the extractive solvent, and the $C_4$ acetylenes to a rectifier column;
separating the crude butadiene product from the crude isoprene product, the extractive solvent and $C_4$ acetylenes in the rectifier column;
feeding the crude butadiene product to a butadiene finishing column;
purifying 1,3-butadiene from the crude butadiene product in the butadiene finishing column;
feeding the crude isoprene product, the extractive solvent and the $C_4$ acetylenes to a degasser column;
separating the extractive solvent from the crude isoprene product and the $C_4$ acetylenes in the degasser column;
feeding the crude isoprene product and the $C_4$ acetylenes to an isoprene finishing column; and
purifying isoprene from the crude isoprene product and the $C_4$ acetylenes in the isoprene finishing column.

14. The process of claim 13, further comprising removing cyclopentadiene present in the $C_5$ hydrocarbon mixture by dimerizing cyclopentadiene to dicyclopentadiene in a dimerization heat exchanger.

15. The process of claim 13, further comprising removing cyclopentadiene present in the $C_5$ hydrocarbon mixture by selective hydrogenation of cyclopentadiene to cyclopentene and cyclopentane.

16. The process of claim 13, further comprising separating propyne from the crude butadiene product in a propyne column.

17. The process of claim 13, further comprising removing the extractive solvent from the crude isoprene product and the $C_4$ acetylenes in an acetylene washer column.

18. The process of claim 13, further comprising feeding the light ends of the $C_5$ hydrocarbon mixture from the $C_5$ purification column and an extractive solvent to a $C_5$ washer column.

19. The process of claim 18, further comprising absorbing isoprene from the $C_5$ hydrocarbon mixture by the extractive solvent in the $C_5$ washer column to generate an overhead product comprising $C_5$ components that are not absorbed by the extractive solvent, a bottom product comprising the extractive solvent, $C_5$ di-olefins, and acetylenes, and a side product comprising isoprene.

* * * * *